(12) United States Patent
Trapp et al.

(10) Patent No.: US 6,478,794 B1
(45) Date of Patent: Nov. 12, 2002

(54) BIPOLAR COAGULATION AND CUTTING DEVICE FOR ENDOSCOPIC SURGERY

(75) Inventors: Rainer Trapp, Graben-Neudorf (DE); Uwe Dux, Au am Rhein (DE)

(73) Assignee: Forschungszenlrum Karlsruhe GmbH, Karlsruhe (DE)

( * ) Notice: Subject to any disclaimer, the term of this patent is extended or adjusted under 35 U.S.C. 154(b) by 0 days.

(21) Appl. No.: 09/654,233

(22) Filed: Sep. 2, 2000

Related U.S. Application Data

(63) Continuation-in-part of application No. PCT/EP99/00214, filed on Jan. 15, 1999.

(30) Foreign Application Priority Data

Jan. 26, 1998 (DE) ......................................... 198 02 743

(51) Int. Cl.⁷ ............................................... A61B 18/18
(52) U.S. Cl. ............................ 606/45; 606/51; 606/167
(58) Field of Search ............................ 606/41, 45, 46, 606/48–52, 167, 170, 171

(56) References Cited

U.S. PATENT DOCUMENTS

| | | | |
|---|---|---|---|
| 2,056,377 A | * 10/1936 | Wappler | 606/48 |
| 5,269,780 A | * 12/1993 | Roos | 606/42 |
| 5,290,287 A | * 3/1994 | Boebel et al. | 606/51 |
| 5,445,638 A | * 8/1995 | Rydell et al. | 606/171 |
| 5,718,703 A | * 2/1998 | Chin | 606/46 |
| 5,891,141 A | * 4/1999 | Rydell | 606/167 |

FOREIGN PATENT DOCUMENTS

| | | |
|---|---|---|
| DE | 40 32 471 | 4/1992 |
| WO | WO 95/13027 | 5/1995 |

* cited by examiner

*Primary Examiner*—Michael Peffley
(74) *Attorney, Agent, or Firm*—Klaus J. Bach

(57) ABSTRACT

In a bipolar coagulation and cutting device for endoscopic surgery with a proximal operating part and a distal grasping part interconnected by a shaft, the distal grasping part includes jaws, each having two spaced branches supported on flexible wires. The jaws are held apart but are movable toward each other by actuating means extending along the shaft for the engagement of tissue between the jaws. HF energy can be supplied for the coagulation of the tissue engaged between the jaws. A wire electrode is also mounted on the shaft so as to be movable by the actuating means between the spaced branches of the jaws for cutting, by HF energy application, the coagulated tissue engaged between the jaws.

6 Claims, 7 Drawing Sheets

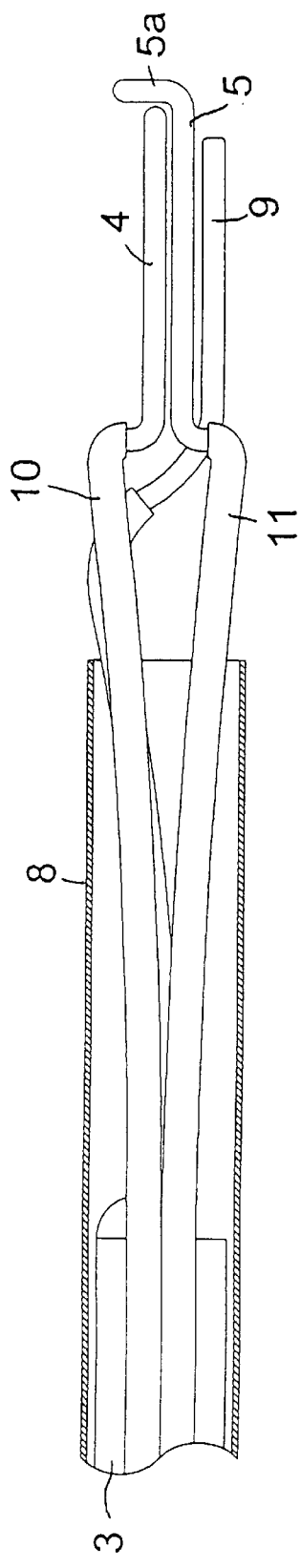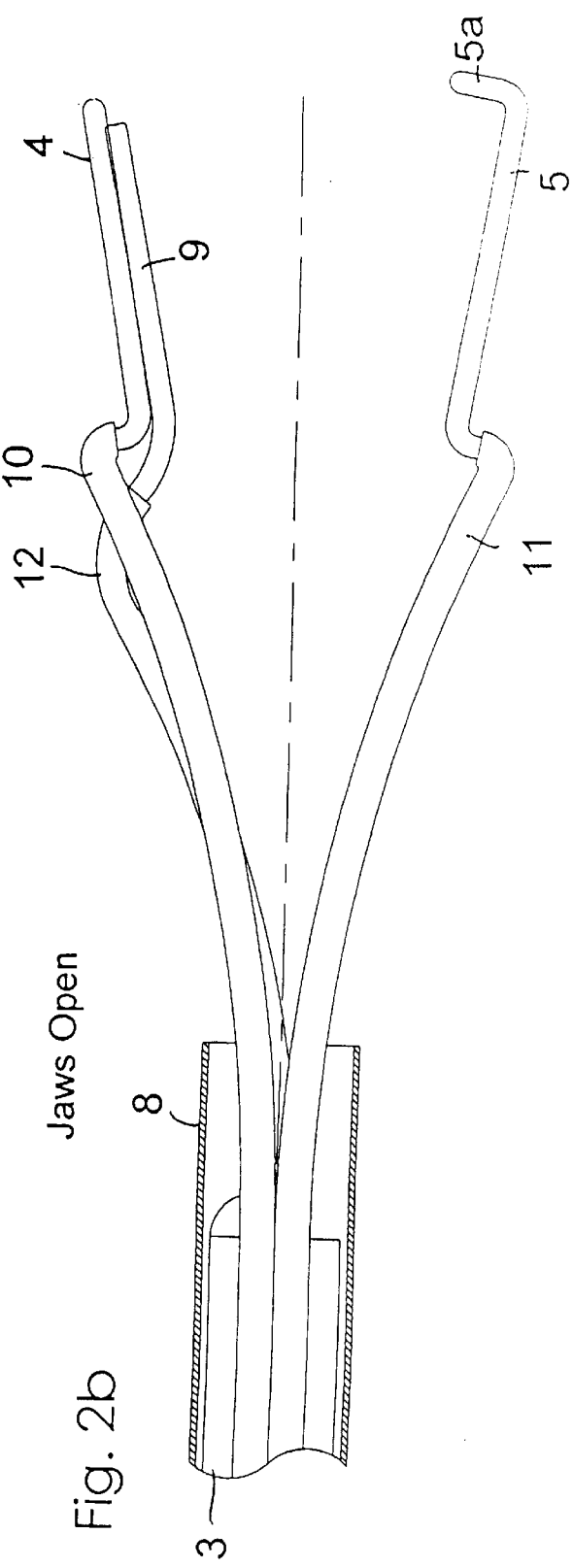

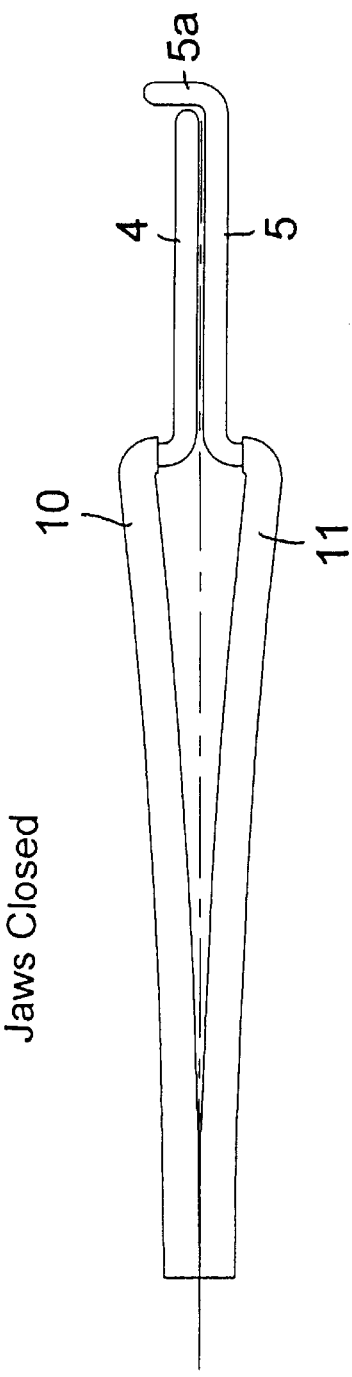
Fig. 3a Jaws Closed
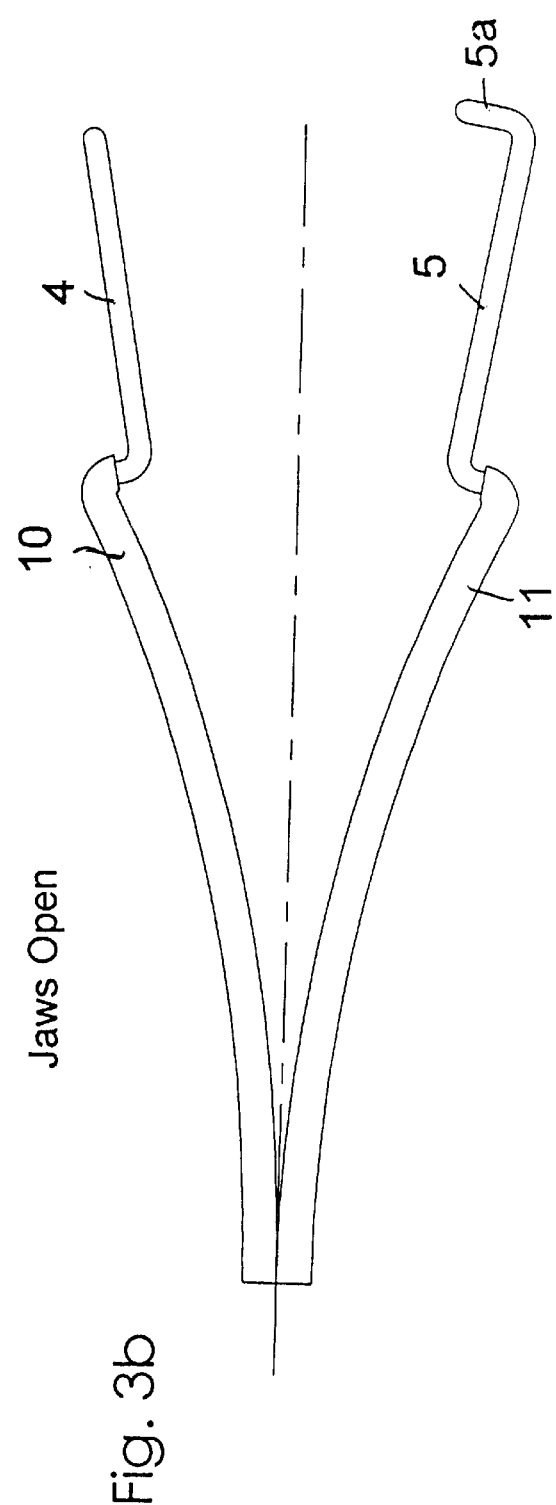
Fig. 3b Jaws Open

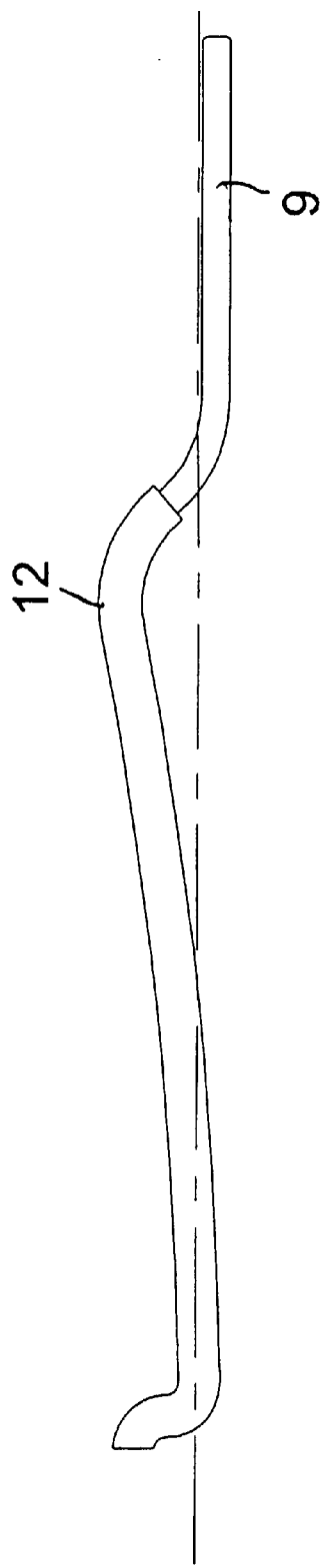
Fig. 4a  Cutting Structure Closed
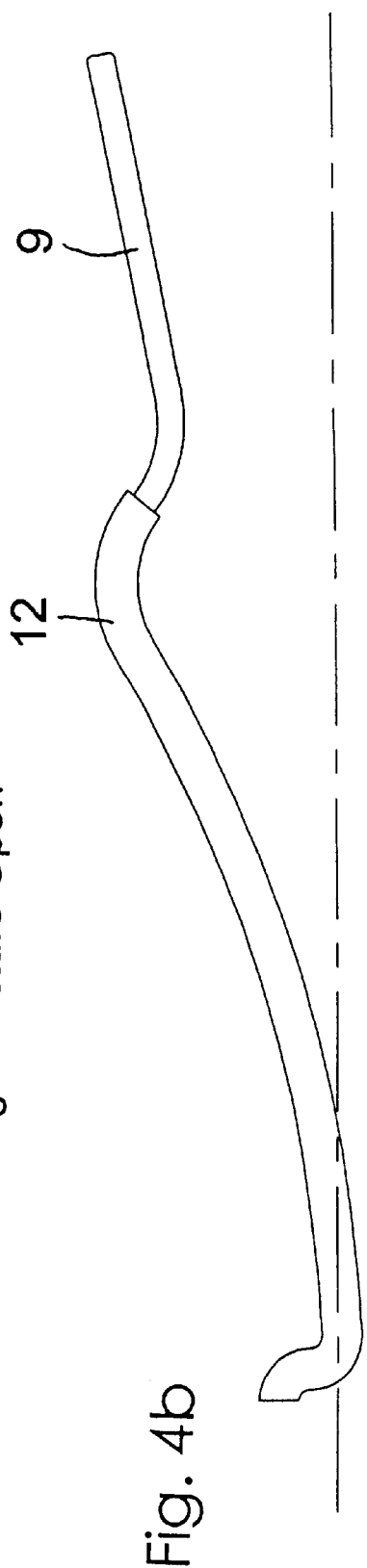
Fig. 4b  Cutting Structure Open

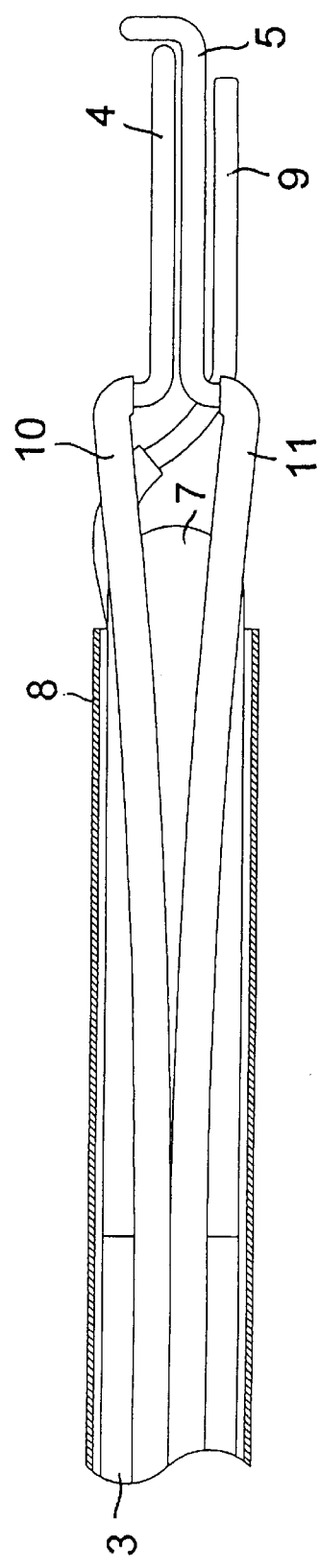
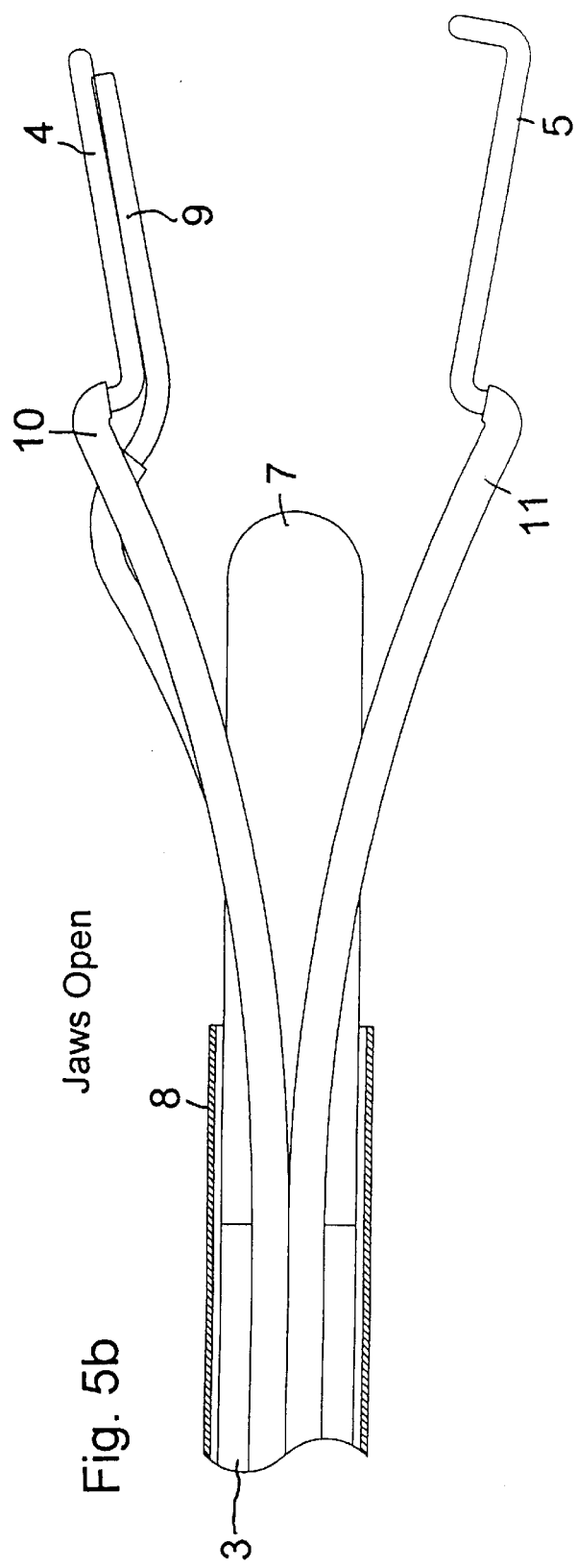
Fig. 5a  Jaws Closed
Fig. 5b  Jaws Open

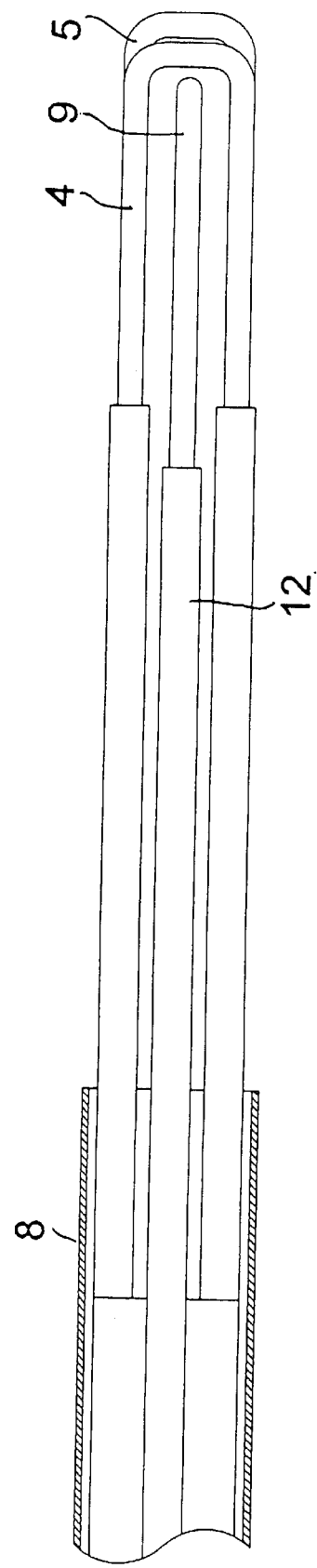
Fig. 6  Straight Jaws (Top View)

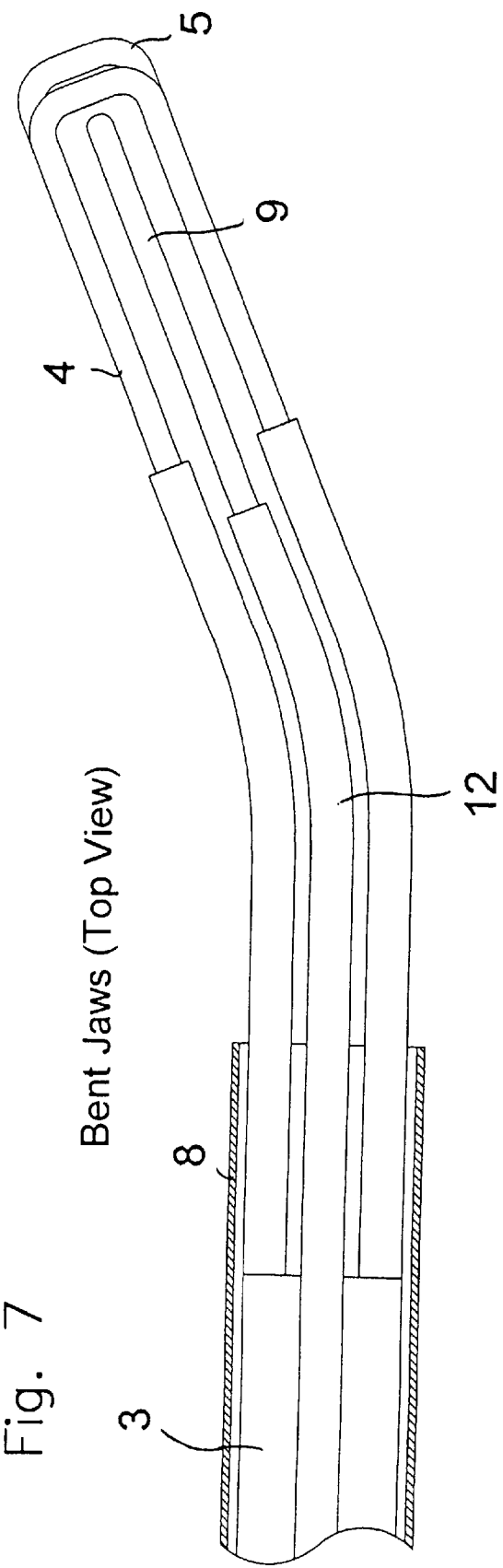

BIPOLAR COAGULATION AND CUTTING DEVICE FOR ENDOSCOPIC SURGERY

This is a continuation-in-part application of International Application PCT/EP99/00214 filed Jan. 15, 1999, and claiming the priority of German application 198 02 743.5 filed Jan. 26, 1998.

BACKGROUND OF THE INVENTION

The invention relates to a bipolar coagulation and cutting device for use in endoscopic surgeries with two U-shaped jaws, which are supported at the end of an operating shaft so as to be movable relative to each other for coagulating tissue engaged between the jaws and a cutting structure for severing the coagulated tissue.

Such a combined instrument is known from the information leaflet of the Cabot Technology Corporation, 2150 Cabot Boulevard West, Langhorne Pa. 19047, USA, which was distributed in 1995. The instrument described therein includes a grasping structure comprising two branches, which are U-shaped and along which tissue is coagulated. Subsequently, a cutting blade is moved forwardly through the grasping and coagulation structure, which cuts the tissue between the coagulated areas.

A combination instrument, which is operated in principle in the same manner, is disclosed in U.S. Pat. No. 5,445,638. Both instruments have in common that the grasping structure is also used for bipolar coagulation and, after coagulation, the intermediate tissue area is cut mechanically by a cutting blade. This procedure is performed by the surgeon. The forces required for the cutting of the tissue have to be transmitted from one end of the instrument to the other.

It is the object of the present invention to provide a combined instrument for the endoscopic surgery with which the tissue is grasped and safely engaged by U-shaped jaws formed by branches and, at the same time, a reliable line coagulation can be performed in accordance with the shape of the branches and, afterwards, the tissue is severed in the coagulated intermediate area between the U-shaped clamp branches by a cutting device requiring minimal force application.

SUMMARY OF THE INVENTION

In a bipolar coagulation and cutting device for endoscopic surgery with a proximal operating part and a distal grasping part interconnected by a shaft, the distal grasping part includes jaws, each having two spaced branches supported on flexible wires. The jaws are held apart but are movable toward each other by actuating means extending along the shaft for the engagement of tissue between the jaws. HF energy can be supplied for the coagulation of the tissue engaged between the jaws. A wire electrode is also mounted on the shaft so as to be movable by the actuating means between the spaced branches of the jaws for cutting, by HF energy application, the coagulated tissue engaged between the jaws.

Preferably, means are provided for guiding the branches of the grasping jaws and of the cutting device in a stable manner. With a blade-like configuration of the cutting electrode, the tissue separation is further facilitated. The two branches of the coagulation structure are curved or wave-like for improved engagement of the tissue. Both branches are disposed on top of one another in parallel when they are pressed together. The branches may be straight or they may be curved. For the safe engagement of the tissue, it is often advantageous if one of the two branches is angled with respect to the other and extends beyond the other branch when the two branches are completely folded together. If one of the branches is angled in a hook-like fashion such that, when folded together, the jaw with the hook-shaped branch overlaps the other, the tissue is firmly engaged by the jaws. Such firm engagement could be obtained with prior art grasping devices only by the provision of corrugations by which the engaged tissue has often been damaged.

The main advantage of the arrangement according to the invention is that, in addition to the grasping and coagulation procedure by high frequency energy application in accordance with the invention, the tissue is also severed by the application of high frequency energy by means of a particularly shaped cutting electrode. This is particularly advantageous for relatively small severing lengths (<5 mm) since a mechanical cutting plate is guided with a relatively high tolerance. It cannot be accurately controlled since, during forward movement of the cutting blade, its position is not easily visible. The surgeon does not need to apply cutting forces with the arrangement according to the invention, and can therefore better concentrate on the guidance and movement of the combined instrument.

With the line-like configuration of the two clamping jaw branches and a corresponding forwardly limited and closed coagulation line impressed into the tissue, the enclosed area can then easily be fully severed. The two branches may be straight or curved and, in addition, both may be wave-shaped. The shape of the two branches may vary in reasonable ways depending on the application.

BRIEF DESCRIPTION OF THE DRAWINGS

FIG. 2a shows the distal end of the instrument with closed jaws,

FIG. 2b shows the distal end of the instrument with open jaws,

FIG. 3a shows the distal end of the instrument with closed jaws,

FIG. 3b shows a grasping jaw structure opened,

FIG. 4a shows the cutting member in a cutting position,

FIG. 4b shows the cutting member in a removed position,

FIG. 5a shows an embodiment of the distal end of the instrument with the jaws closed and guided by a tongue, FIG. 5b shows the end of the shaft with the tongue forming a guide element for the jaws shown in an open position, FIG. 6 is a top view of the distal end of the instrument with straight jaws, and FIG. 7 is a top view of the distal end of the instrument with bent-over jaws.

DESCRIPTION OF PREFERRED EMBODIMENTS

Figure 1:
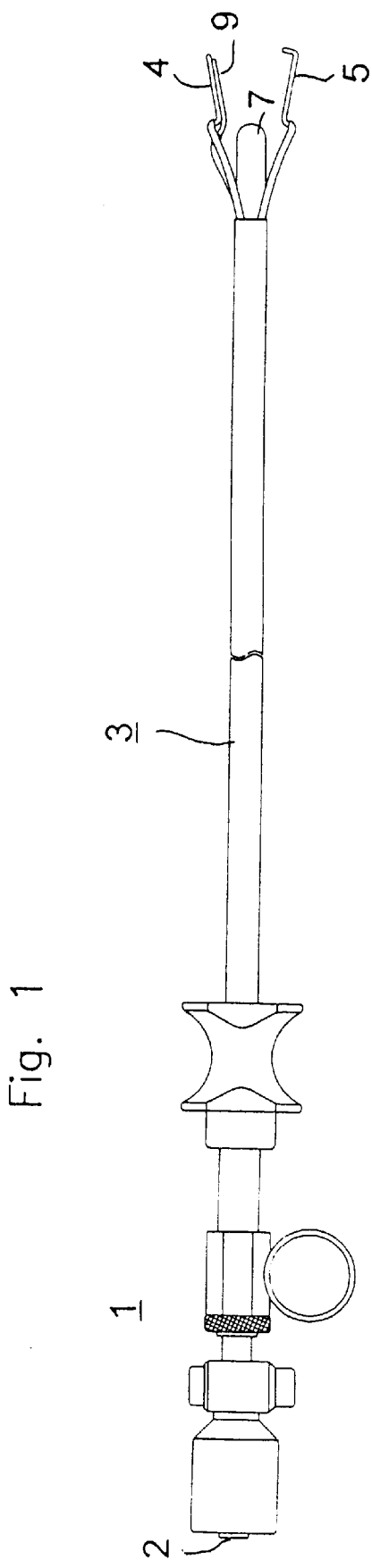
FIG. 1 shows the complete instrument.

FIG. 1 shows the whole endoscopic coagulation and cutting instrument. At the proximal end of the instrument shown at the left-hand side of FIG. 1, there is the operating part with electrical connections 2 for the high frequency energy supply. The intermediate area 3 is formed by a telescopic shaft through which actuating elements and other devices or structures needed for the operation of the instrument extend. At the right end, that is, at the distal end, the shaft 3 carries a grasping structure including jaws 4 and 5. FIGS. 2a and 2b show the instrument with the jaws 4 and 5 in a closed and an open position, respectively. The guide tongue is eliminated in these figures as they are intended only to clearly show the jaw elements. When the jaws are open, they are moved over the tissue to be grasped so that the tissue is diposed between the jaws. Then the sleeve 8, which is axially movably disposed on the shaft 3 is moved forwardly thereby engaging the two flexible jaw support arms 10 and 11 and moving the jaws 4 and 5 toward each other. The tissue disposed between the two jaws is engaged thereby and is subjected to high frequency energy for coagulation along the contour of the two jaw branches. After coagulation, the sleeve 7 is still further moved forwardly so as to move the support arm 12 of the cutting electrode 9, through the tissue area delimited by the coagulation line formed by the jaws for cutting the tissue.

As shown in FIGS. 2a and 2b, the end of the jaw 5 may have an angled hook-like end portion 5a for better engaging the tissue. The two jaw branches and the, with respect to the shaft axis, mirror-reversed unidirectional curvature of the respective guide wires is shown in FIGS. 3a and 3b. FIG. 3a shows the jaws in a closed position and FIG. 3b shows the jaws open. The figures show that, with the given shape of the jaw branches, the tissue can be firmly grasped. FIGS. 4a and 4b show the cutting electrode 8. FIG. 4a shows the cutting electrode 9 in a cutting position and FIG. 4b shows the cutting electrode 9 in an open position.

FIGS. 5a and 5b show the distal end of the shaft in a cross-sectional view in order to show the guide features of the guide tongue which is rigidly connected to the shaft at the distal end thereof. The wires for supplying the HF energy to the coagulation pliers jaws 4, 5 are disposed at one side of the guide tongue 7, whereas the wires for supplying the energy to the cutting electrode 9 are disposed at the other side of the guide tongue 7. The simple line-like arrangement of the two jaws 4, 5 is apparent from FIG. 6, which is a top view. The figures show the jaws in one particular way, that is, in a U-shape wherein they are closed at the front. Other shapes are possible. In the shown embodiment, the cutting electrode is disposed in the center of the jaw branches, which is necessary for the cutting between the coagulation lines.

FIG. 7 shows the operating area, that is, the jaws bent over to one side. With this arrangement, the operating area is moved to the side of the axis of the shaft and provides for better viewing of the tissue being treated by the surgeon.

All materials—metallic or non-metallic materials—of which the instrument consists are tissue compatible and are admitted for use in connection with medical operations. They are acceptable and suitable particularly with regard to cleaning and sterilization procedures. Furthermore, the electrical structures are isolated with respect to a patient such that no current from the instrument can flow through parts of a patient's body.

What is claimed is:

1. A bi-polar coagulation and cutting device for endoscopic surgery comprising: a proximal operating part, a shaft part connected at one end to said operating part and a distal grasping part connected to the other end of said shaft part and including jaws which are movable toward, and away from, each other by axial movement of said shaft or part thereof for the engagement and coagulation of tissue engaged therebetween, each of said jaws including two spaced branches, a cutting structure disposed between the two spaced branches of the jaws for cutting the tissue in the space between the two branches after coagulation of that tissue, each of said branches being disposed at the end of an elastic support wire disposed in said shaft and being curved so as to normally bias said jaws away from each other and a wire electrode formed at one end of an elastic wire also disposed in said shaft and being disposed between the elastic support wires of said spaced branches of one of said jaws and being bent further outwardly than the support wires carrying said jaw branches so that, when said sleeve is advanced, first said jaws are pressed together for the engagement of tissue therebetween and, upon further advancement of said sleeve, said wire electrode is moved inwardly through the space between said jaw branches and against tissue engaged therebetween, which tissue is cut by said electrode when high frequency power is supplied to said electrode.

2. A bipolar coagulation and cutting device according to claim 1, wherein a tongue is mounted onto the distal end of said shaft so as to project therefrom axially, but not further than up to the distal end of said jaws, said tongue forming a guide structure for said elastic support wires.

3. A bipolar coagulation and cutting device according to claim 2, wherein said cutting electrode is ground to form a knife-like edge at the side adjacent said tissue to be cut.

4. A bipolar coagulation and cutting device according to claim 3, wherein the branches of said jaws are wave-like in their shape.

5. A bipolar coagulation and cutting device according to claim 4, wherein said branches of said jaws are so supported that their engagement areas at the distal end of said elastic wires extend parallel when said branches are compressed.

6. A bipolar coagulation and cutting device according to claim 5, wherein one of said jaws has a distal end portion which is angled by 90° toward the other jaw and said angled end portion overlaps the other jaw when the jaws are pressed together.

* * * * *